US00PP36587P2

(12) United States Plant Patent
Bacon et al.

(10) Patent No.: US PP36,587 P2
(45) Date of Patent: Apr. 8, 2025

(54) PEACH TREE NAMED 'SUPECH28'

(50) Latin Name: *Prunus persica*
Varietal Denomination: SUPECH28

(71) Applicant: Sun World International, LLC, Bakersfield, CA (US)

(72) Inventors: Terry A. Bacon, Maplewood, NJ (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 18/763,102

(22) Filed: Jul. 3, 2024

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./194, 197, 198
See application file for complete search history.

*Primary Examiner* — Susan McCormick Ewoldt
(74) *Attorney, Agent, or Firm* — Knobbe, Martens, Olson & Bear, LLP

(57) ABSTRACT

The new variety of peach tree 'SUPECH28' is characterized by having large-size fruit with a dark red over-color and yellow flesh. The fruit ripens very early and has a strong adherence of the stone to the flesh.

1 Drawing Sheet

Latin name of the genus and species claimed: *Prunus persica.*

Variety denomination: 'SUPECH28'.

BACKGROUND AND SUMMARY OF THE INVENTION

This invention relates to the discovery and asexual propagation of a new and distinct variety of peach, *Prunus persica* cv. 'SUPECH28'. The variety 'SUPECH28' was originated by hybridization and was first selected in May 2016 by Terry A. Bacon and Terrence J. Frett as breeder number: 'PE1807'. The new variety was first evaluated by Terry A. Bacon and Terrence J. Frett near Wasco, California in Kern County.

The seed parent is 'Supechseventeen' (U.S. Plant Pat. No. 22,588) and the pollen parent is an unknown member of a bulk pollen of four peach varieties: 'PE1298' (unpatented), 'Supechtwenty' (U.S. Plant Pat. No. 26,500), 'PE1318' (unpatented), and 'Supechnineteen' (U.S. Plant Pat. No. 26,525). The parent varieties were first crossed in February 2012, with the date of first sowing being February 2013, and the date of first flowering being February 2015. The new peach variety 'SUPECH28' was first asexually propagated by Terry A. Bacon and Terrence J. Frett near Wasco, Kern County, California in February 2017 by dormant grafting.

The new variety 'SUPECH28' is characterized by having large-size fruit with a dark red over-color and yellow flesh. The fruit ripens very early and has a strong adherence of the stone to the flesh.

The new variety 'SUPECH28' is distinguished from its seed parent 'Supechseventeen' (U.S. Plant Pat. No. 22,588) in that blooming of the new variety starts about February 7$^{th}$ and ripening starts about April 21$^{st}$, compared to February 11$^{th}$ and May 1$^{st}$ respectively for 'Supechseventeen'. Further, fruit of the new variety has a lower weight, at about 145 g compared to 180 g for 'Supechseventeen'.

The new variety 'SUPECH28' can be distinguished from each of the four peach varieties of the bulk pollen from which the pollen parent was derived: 'PE1298' (unpatented), 'Supechtwenty' (U.S. Plant Pat. No. 26,500), 'PE1318' (unpatented), and 'Supechnineteen' (U.S. Plant Pat. No. 26,525). The fruit of the new variety 'SUPECH28' ripens earlier (April 21) than the fruit of each of 'PE1298' (May 2), 'Supechtwenty' (April 29), 'PE1318' (May 12), and 'Supechnineteen' (May 2). Further, the new variety 'SUPECH28' has a fruit weight of 145 g, compared to a fruit weight of 185 g for 'Supechnineteen', a fruit weight of 155 g for 'PE1318', a fruit weight of 184 g for 'Supechtwenty', and a fruit weight of 152 g for 'PE1298'.

The new variety 'SUPECH28' has a Brix: acid ratio of 15 compared to a Brix:acid of 30 for 'Supechnineteen', 13 for 'PE1318', 13 for 'Supechtwenty', and 13 for 'PE1298'. Additionally, the new variety 'SUPECH28' has a lower fruit acidity at 0.8 compared to 0.95 for 'PE1318', 0.95 for 'PE1298', and higher than 'Supechnineteen' at 0.40 and 'Supechtwenty' at 0.45.

Lastly, the flesh of the new variety 'SUPECH28' is yellow, similar to the flesh color of 'PE1318', 'Supechtwenty', and 'PE1298', but different from the white flesh color of 'Supechnineteen'.

The new variety 'SUPECH28' resembles 'Supechseventeen' (U.S. Plant Pat. No. 22,588), 'Supechtwentytwo' (U.S. Plant Pat. No. 30,979), 'Supechfifteen' (U.S. Plant Pat. No. 13,177), 'Supechtwentyone' (U.S. Plant Pat. No. 26,773), and 'Super Rich' (U.S. Plant Pat. No. 9,860) in that the fruit of all varieties have yellow-colored flesh. However, the new variety 'SUPECH28' ripens earlier, on April 21$^{st}$, compared to May 1$^{st}$ for 'Supechseventeen', May 3$^{rd}$ for 'Supechtwentytwo', May 5$^{th}$ for 'Supechfifteen', May 11$^{th}$ for 'Supechtwentyone', and May 4$^{th}$ for 'Super Rich'. Additionally, the fruit of the new variety 'SUPECH28' has a lower weight, at 145 g compared to a weight of 180 g for 'Supechseventeen', a weight of 172 g for 'Supechtwentytwo', a weight of 185 g for 'Supechfifteen', and a weight of 185 g for 'Supechtwentyone'. However, the fruit of the new variety 'SUPECH28' is heavier that of 'Super Rich' (135 g).

Lastly, the new variety 'SUPECH28' has a Percent Brix of 12% and Brix:Acid ratio of 15, compared to a Percent Brix of 13% and a Brix:Acid of 14 for 'Supechseventeen', a Percent Brix of 13% and a Brix:Acid of 16 for 'Supechtwentytwo', a Percent Brix of 11% and a Brix:Acid of 11 for 'Supechfifteen', a Percent Brix of 13% and a Brix:Acid of 14 for 'Supechtwentyone', and a Percent Brix of 11% and a Brix:Acid of 12 for 'Super Rich'.

The new variety 'SUPECH28' has been shown to maintain its distinguishing characteristics through successive asexual propagations by, for example, cuttings and grafting.

BRIEF DESCRIPTION OF THE DRAWING

The accompanying color photographic illustration taken from a 6-year-old plant shows typical specimens of the foliage and fruit of the present new peach variety 'SUPECH28'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, Sixth edition, 2015.

The descriptive matter which follows pertains to 4-year-old 'SUPECH28' trees grown in the vicinity of Wasco, Kern County, California, during 2023, and is believed to apply to plants of the variety grown under similar conditions of soil and climate elsewhere.

TREE

General: (Measurements taken on 3-year-old trees unless otherwise noted.).

- *Size*.—Medium. Reaches a height of approximately 3 meters with normal pruning.
- *Vigor*.—Strong. Top shoot growth of about 1.5 meters during the first growing season.
- *Growth*.—Semi-spreading.
- *Type of bearing*.—On one year old shoots.
- *Productivity*.—Very productive. About 640, 25 lb cartons per acre. Thinning and spacing of fruit is necessary.
- *Fertility*.—Self-compatible.
- *Hardiness*.—Hardy in all fruit growing areas of California; winter chilling requirement is approximately 200 hours at or below 7.2° C.
- *Disease resistance/susceptibility*.—No specific testing for relative plant disease resistance/susceptibility has been undertaken. Under close observation in Kern County, California, no particular plant/fruit disease resistance/susceptibility has been observed.

Trunk: (Measurements taken at approximately 30 cm above the soil line.).

- *Diameter*.—Approximately 16 cm.
- *Texture*.—Medium shaggy, increases with the age of the tree.
- *Trunk color*.—About Light Greyed-Green 198D with highlights of Medium Greyed-Orange 182A, becoming darker with age.

Branches: (Measurements taken at approximately 90 cm above the soil line.).

- *Size*.—Approximately 12 cm.
- *Texture*.—Medium shaggy; increasing with tree age.
- *Color*.—About Medium Grey 201D with highlights of Medium Greyed-Orange 182B, becoming darker with age.
- *Lenticels density*.—Medium, approximately 1-3 per $cm^2$.
- *Lenticels color*.—About Medium Grey 201D.
- *Lenticels length*.—Approximately 5 mm.
- *Lenticels width*.—Approximately 1.2 mm.

One year old shoots: (Data taken in May at midpoint of current-season growth.).

- *Size*.—Average diameter approximately 5 mm.
- *Type of bearing*.—Even and every year.
- *Color*.—Topside: About Medium Yellow-Green 146C. Underside: About Medium Yellow-Green 146C.
- *Internode length*.—Approximately 2-3 mm, midway in shoot.
- *Lenticels density*.—Medium; about 8 per $cm^2$.
- *Lenticels color*.—About Medium Grey 201D.
- *Lenticel dimensions*.—Approximately 1.0 mm long by 0.2 mm wide.
- *Presence of anthocyanin coloration*.—Not Present.
- *Density of flower buds*.—Medium, two per node.

Vegetative buds:

- *Position of vegetative bud in relation to shoot*.—Slightly held out.
- *Bud size*.—Approximately 5 mm long by 2.5 mm wide.
- *Bud shape*.—Conical.
- *Color*.—About Dark Greyed-Orange 177A.

Flower buds:

- *Bud dimensions*.—Approximately 3 mm long by 2 mm wide.
- *Bud shape*.—Ovoid.
- *Color*.—About Dark Greyed-Orange 177A.
- *Ratio of flower buds to vegetative buds*.—2 flower buds: 1 vegetative bud.

FOLIAGE

Leaves: (Data taken in July on fully expanded leaves at midpoint of current-season growth).

- *Average length*.—Medium; approximately 140 mm without petiole.
- *Average width*.—Medium; approximately 41 mm.
- *Length:width ratio*.—Medium; about 3.4:1
- *Time of leaf bud burst*.—Early, around balloon stage. Approximately February 3$^{rd}$.
- *Shape*.—Elliptic.
- *Color of upper side*.—About Dark Green 139A.
- *Color of lower side*.—About Dark Green 138B.
- *Angle of base*.—Acute.
- *Angle at apex*.—Acute and small.
- *Venation*.—About 1 cm apart, evenly distributed over the leaf.
- *Venation pattern*.—Pinnate.
- *Vein color*.—About Light Green 139D.
- *Presence of red coloration of mid-vein on the lower side*.—Absent or very sparse.

*Surface texture*.—Smooth on both top and bottom surfaces.
*Shape in the cross section*.—Flat.
*Leaf blade tip*.—Curved downwardly.
*Density of pubescence for lower side*.—Not pubescent.
*Incisions of margin*.—Crenate.

Petiole:
*Average length*.—Medium; approximately 9 mm.
*Average diameter*.—Approximately 2 mm.
*Color*.—About Medium Green 139C.

Stipules:
*Number/leaf bud*.—Usually 2.
*Typical length*.—Medium, approximately 11 mm.
*Color*.—About Dark Greyed-Orange 166A when dried.
*Persistence*.—Falls off.

Leaf glands:
*Form*.—Globose.
*Average number and arrangement*.—Usually 0-2, alternating. Predominately on petiole.
*Dimensions*.—Approximately 1 mm long by 0.8 mm wide.
*Color*.—About Dark Greyed-Yellow 162A, becoming Dark Greyed-Orange 166A over time.

FLOWERS

General:
*Time of beginning of flowering*.—Very early for the San Joaquin Valley, California.
*Flower blooming period*.—First Bloom: Approximately February 7. Full Bloom: Approximately February 11.
*Location of first bloom*.—Tips of one year old shoot.
*Location of full bloom*.—Central part of the tree canopy.
*Duration of bloom*.—Approximately 10 days.
*Diameter*.—Approximately 28 mm.
*Form*.—Showy.
*Aroma*.—Slight.

Pedicels:
*Length*.—Approximately 3 mm.
*Width*.—Approximately 2 mm.
*Color*.—About Medium Green 138B.

Sepals:
*Number*.—5.
*Shape*.—Medium ovate.
*Position*.—Adpressed to petals.
*Length*.—Approximately 5 mm.
*Width*.—Approximately 3 mm.
*Surface texture*.—Smooth.
*Color*.—About Dark Greyed-Purple 184A.

Petals:
*Number*.—5.
*Arrangement*.—Touching.
*Color*.—About Light Pink 54D.
*Surface texture*.—Smooth.
*Length*.—Approximately 13 mm.
*Width*.—Approximately 7 mm.
*Shape*.—Medium elliptic.
*Apex shape*.—Rounded.
*Base shape*.—Narrows at point of attachment.
*Undulation of margins*.—Medium.
*Frequency of flowers with double petals*.—Never.
*Claw*.—Partially developed.

Stigma:
*Position compared to anthers*.—Above.

Stamens:
*Number*.—About 40.
*Length*.—Variable, ranging from 7 mm to 10 mm.
*Filament color*.—About White 155A with highlights of Light Pink 54D.
*Pollen*.—Present.
*Flower pollen color*.—About Medium Greyed-Orange 166C.
*Position compared to petals*.—At the same level.

Anthers:
*Pollen*.—Present.

Ovary:
*Pubescence*.—Present.

Pistil:
*Length*.—Approximately 17 mm.
*Ovary diameter*.—Approximately 2 mm.
*Frequency of supplementary pistils*.—Few.
*Stigma position in relation to anthers*.—Above.

Receptical:
*Depth*.—Medium, about 4 mm.
*Pubescence of inner surface* (*at pink bud stage*).—Absent.
*Pubescence of outer surface*.—Present.

FRUIT

General: (Description taken at firm-mature near Wasco, Kern County, California).
*Time of beginning of fruit ripening*.—Very early.
*Date of first pick*.—Approximately April 21.
*Date of last pick*.—Approximately May 1.

Peduncle:
*Length of stem*.—Approximately 7 mm.
*Diameter of stem*.—Approximately 3 mm.
*Color of stem*.—About Light Green 139D.

Fruit size:
*Size*.—Large; about 145 g.
*Height*.—Approximately 68 mm.

Fruit shape:
*Shape viewed from apex*.—Circular, some fruit with prominent suture.
*Shape in lateral view, perpendicular to suture*.—Circular.
*Shape ventral side, facing suture*.—Medium oblate.
*Symmetry viewed from pistil end*.—Moderately asymmetric.
*Shape of pistil end*.—Weakly depressed.
*Mucron tip at pistil end*.—Occasionally present.
*Depth of stalk cavity*.—Medium; about 7 mm.
*Width of stalk cavity*.—Medium; about 7 mm.
*Promenence of suture*.—Medium.

Fruit skin:
*Thickness*.—Medium.
*Adherence to flesh*.—Strong.
*Taste*.—Neutral.
*Surface texture*.—Smooth.
*Reticulation*.—Absent.
*Tendency to crack*.—None.
*Density of pubescence*.—Slight.
*Density of pubescence of skin*.—Medium.
*Ground color*.—About Medim Yellow-Orange 16B.
*Relative area of overcolor*.—Very large, about 90% +.
*Overcolor color of skin*.—About Dark Red 46B to Dark Red 46A.
*Pattern of overcolor of skin*.—Solid.

Flesh:

*Ripens*.—Evenly.

*Color*.—About Medium Yellow-Orange 14C.

*Anthocyanin coloration of flesh next to skin*.—Absent or very weak.

*Anthocyanin coloration of flesh in central part of flesh*.—Absent or very weak.

*Anthocyanin coloration of flesh around stone*.—Absent or very weak.

*Texture*.—Melting.

*Flavor*.—Sweet, with slight acidity and medium aroma.

*Firmness*.—Firm; typically 10 lb pressure at harvest.

*Juiceness*.—Medium; able to squeeze free juice easily.

*Sweetness*.—Medium; about 12% brix at harvest.

*Acidity*.—Medium; about 0.80% titratable acidity.

*Adherence to stone*.—Strong.

*Flesh type*.—Melting.

*Amount of fiber*.—Moderate.

Stone:

*Stone size*.—Medium. Length: Approximately 33 mm. Diameter Facing Suture: Approximately 19 mm. Diameter Perpendicular to Suture Plane: Approximately 25 mm.

*Stone color*.—About Medium Greyed-Yellow 161B when dried.

*Anthocyanin color*.—Absent.

*Intensity of brown color*.—Light.

*Position of maximum*.—Middle.

*Shape in lateral view*.—Medium elliptic.

*Shape in ventral view*.—Narrow elliptic.

*Shape in basal view*.—Medium elliptic.

*Base shape*.—Nearly straight.

*Apex shape*.—Slight point at tip.

*Ridges*.—Rounded throughout.

*Outgrowing keel*.—Partially developed.

*Fibers*.—Not visible.

*Symmetry in lateral view*.—Symmetric or slightly asymmetric.

*Width of stalk end*.—Narrow.

*Tendency to split*.—Low.

*Adherence to flesh*.—Strong.

What is claimed is:

1. A new and distinct variety of peach tree named 'SUPECH28' as herein described and illustrated.

* * * * *

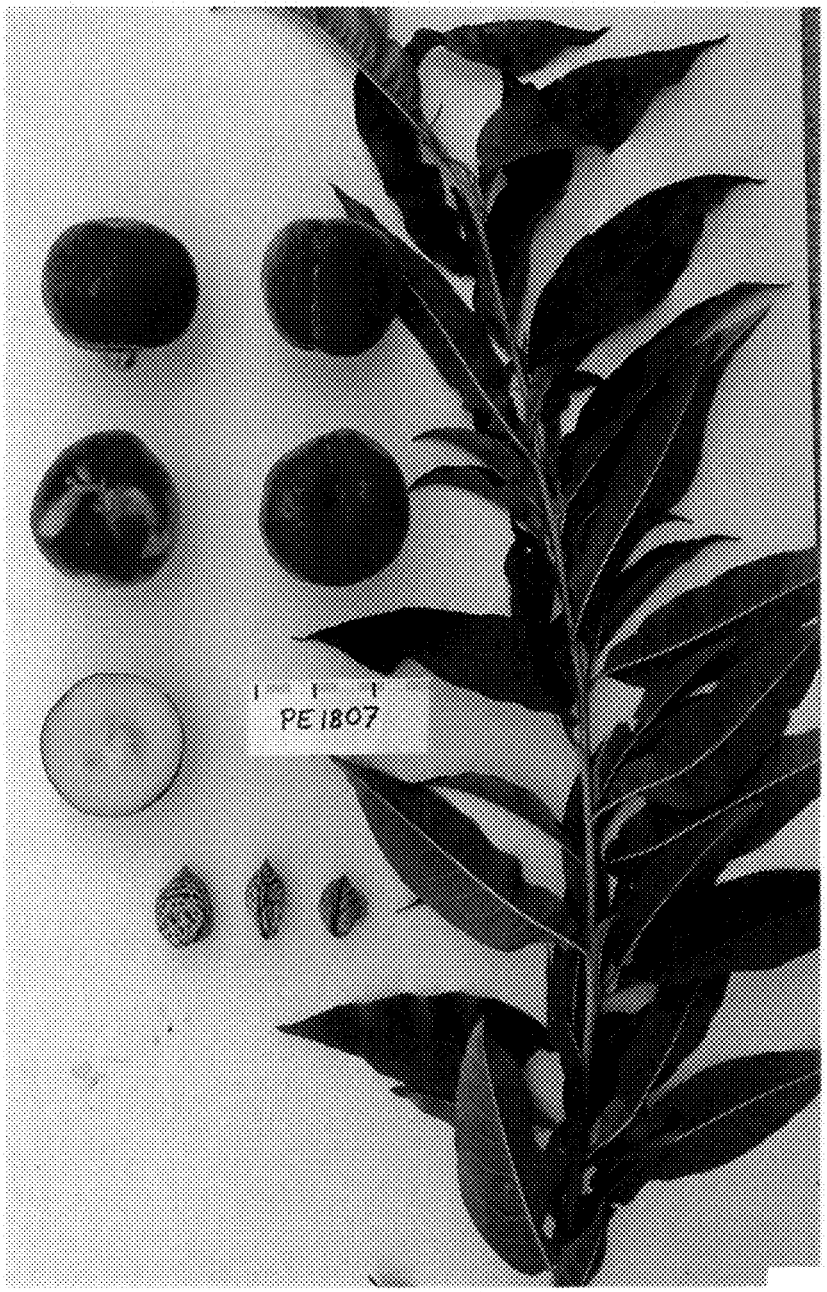
PE 1807